(12) United States Patent
Brungardt

(10) Patent No.: US 12,214,273 B1
(45) Date of Patent: Feb. 4, 2025

(54) VIRTUAL MEASUREMENT SYSTEM FOR ATHLETIC PERFORMANCE TESTING

(71) Applicant: Brett Brungardt, Horseshoe Bay, TX (US)

(72) Inventor: Brett Brungardt, Horseshoe Bay, TX (US)

( * ) Notice: Subject to any disclaimer, the term of this patent is extended or adjusted under 35 U.S.C. 154(b) by 0 days.

(21) Appl. No.: 18/423,141

(22) Filed: Jan. 25, 2024

(51) Int. Cl.
  *A63B 71/06* (2006.01)
  *A63B 24/00* (2006.01)

(52) U.S. Cl.
  CPC .. *A63B 71/0622* (2013.01); *A63B 2024/0025* (2013.01); *A63B 2071/0641* (2013.01); *A63B 2071/0694* (2013.01); *A63B 2214/00* (2020.08); *A63B 2220/05* (2013.01); *A63B 2220/13* (2013.01); *A63B 2220/62* (2013.01); *A63B 2220/806* (2013.01)

(58) Field of Classification Search
  CPC ........ A63B 2071/0641; A63B 71/0622; A63B 2024/0025; A63B 2071/0694; A63B 2220/05; A63B 2214/00; A63B 2220/62; A63B 2220/13; A63B 2220/806
  See application file for complete search history.

(56) References Cited

U.S. PATENT DOCUMENTS

| | | | |
|---|---|---|---|
| 2014/0210856 A1* | 7/2014 | Finn .................... | H04N 13/275 345/633 |
| 2017/0314934 A1* | 11/2017 | Averbuch ............... | G01S 19/50 |
| 2019/0377345 A1* | 12/2019 | Bachrach .............. | B64C 39/024 |
| 2021/0112238 A1* | 4/2021 | Bylicka ................... | G06T 7/292 |

* cited by examiner

*Primary Examiner* — Muhammad N Edun
(74) *Attorney, Agent, or Firm* — HAYNES AND BOONE, LLP

(57) ABSTRACT

A system that includes a mobile application to create a virtual overlay over a field of view of a mobile device, to virtually measure athletic performance of an athlete performing a sports activity. The system is configured to enable virtual boundary-based measurements in order to objectively assess athletes based on scores calculated using the virtual measurements. Displayed to the user are virtual boundaries including virtual planes extending from one or more floor markers within a mobile camera field of view.

16 Claims, 9 Drawing Sheets

VIRTUAL MEASUREMENT SYSTEM FOR ATHLETIC PERFORMANCE TESTING

BACKGROUND

Coaches and/or other athletic professionals often perform athletic performance assessments for athletes, in order to understand how the athlete is responding to various training or coaching methods. These assessments are often cost-prohibitive in terms of required equipment and labor costs. Even when conducted, these assessments may not produce reliable and accurate assessments of the athlete. This may result in frustration by both coach and athlete due to a lack of targeted training, or in the case of inaccurate testing, due to wasted time and resources spent on conducting the assessments. Without properly conducted assessments, coaches, athletes, or other athletic professionals may not be able to objectively compare athletes to one another in standardized activities related to a sport. Coaches of individual sports may not be able to use the objective skill levels of their athlete to plan specialized trainings where necessary and athletes may not be able to gauge the effectiveness of their coaches.

A virtual measurement method for athletic performance testing is needed that allows an athlete's performance to be measured while performing various standardized activities related to a given sport, and also that allows the measured results to be objectively compared to other athletes.

DETAILED DESCRIPTION

A Virtual Measurement System for Athletic Performance Testing ("VMSAPT") uses a mobile device camera or other visual capturing or recording device to measure and record the performance of an athlete undergoing testing of standardized protocols related to a selected test. A standardized score derived from these measurements may be used for reliably measuring athletic performance, objective benchmarking for physical development, and validating on-field performance and back-to-play parameters. Examples of back-to-play parameters are threshold parameters that indicate an athlete is capable of or cleared to return to play. In some embodiments, the back-to-play parameters measure an athlete's mobility, flexibility, strength, or other fitness related metric.

Current methods of measuring and testing athletic performance rely on processes and equipment that are both time and resource-extensive, and may be inaccurate due to subjective methods of measurement. Further, the equipment needed for these current methods may be expensive, and require specially trained in-person crews in order to conduct the testing. There are often instances where a coach and/or athlete would like to regularly test their performance in order to learn where further training or coaching is needed, but the high costs, of time, money, and manpower needed for such assessments is prohibitive. This often results in frustration as coaches and athletes have a finite amount of time in which to train, coach, and develop their athletic skills further. In team sports, there may be tight team schedules that may further limit and/or effect training and coaching time of individual athletes on the team.

The VMSAPT described herein allows a coach or test administrator to virtually measure and test an athlete's performance as the athlete performs various activities preselected for a given sport. The setup and assessment itself can be conducted by a user or test administrator of a mobile device and the athlete, reducing the overall costs necessary for performance assessments. Further, the system and measurement method produce accurate, repeatable measurements for every activity being tested in a given assessment.

Figure 1:
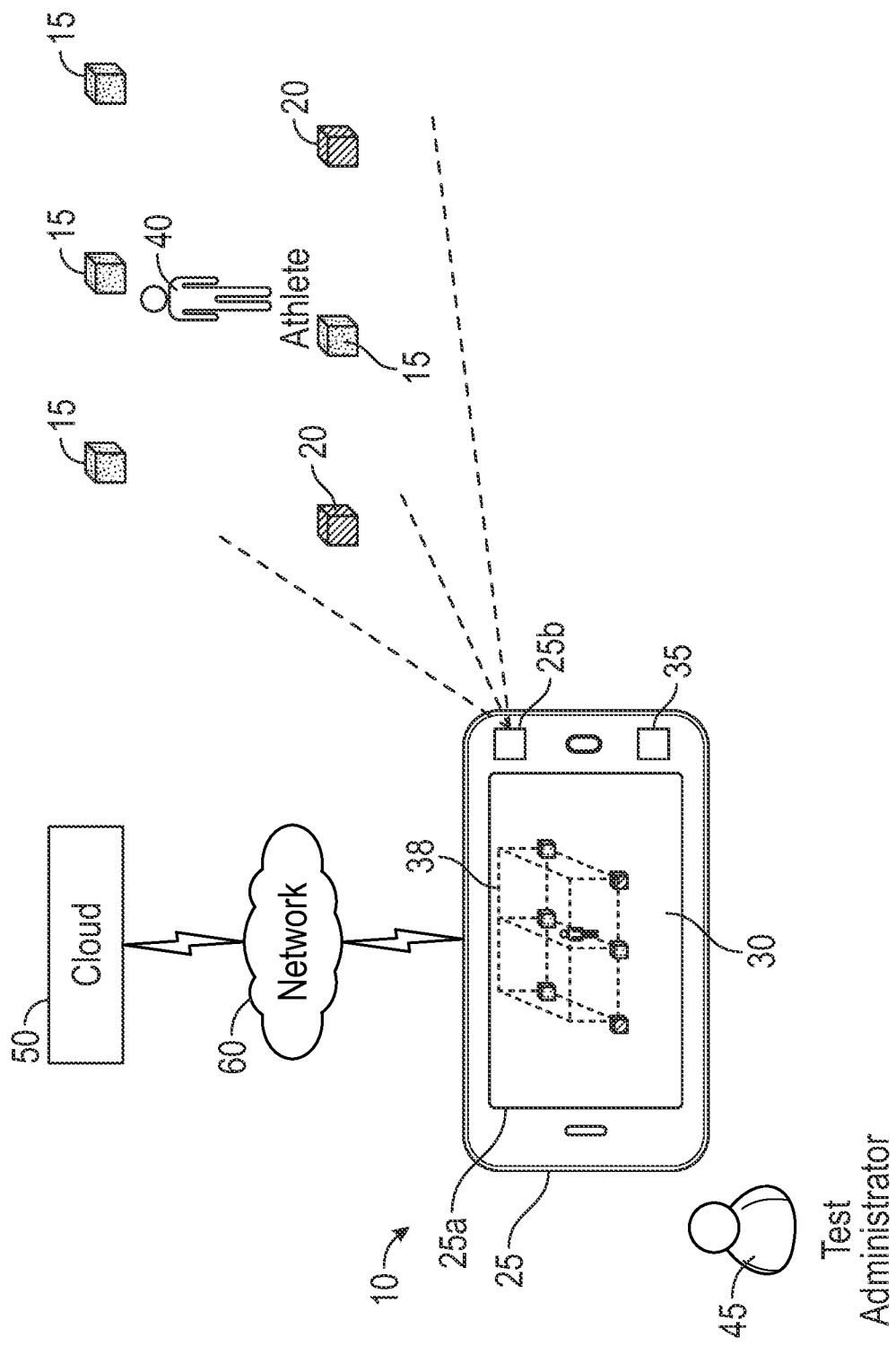
FIG. 1 is a diagrammatic illustration of an athletic performance measurement system that includes a mobile device and floor markers, according to an example embodiment.

In an example embodiment, referring to FIG. 1, an example embodiment of the VMSAPT is illustrated and designated by the numeral 10. In an example embodiment, the system 10 includes floor marker(s) 15, LED light(s) 20, and a mobile device 25. Generally, the mobile device 25 includes a graphical user interface ("GUI") 25a that is capable of displaying a field of view 30 associated with a camera 25b of the mobile device 25. A mobile application 35 is stored in the mobile device 25 and creates a virtual overlay 38 that is displayed over the field of view 30 via the GUI 25a. When the floor marker(s) 15 and the LED light(s) 20 are positioned within the field of view 30 of the camera 25b, the mobile application 35 displays the virtual overlay 38 on the field of view 30 and measures activities of the athlete relative to the virtual overlay 38. A test administrator 45 can aid in the testing procedure. The application 35 is capable of creating a video of the activity that is captured by the camera 25b and application 35 and/or is also capable of calculating scores relating to the activity, both of which can be uploaded or stored in the cloud 50 via a network 60 that is in communication with the cloud 50 and the mobile device 25.

Figure 2:
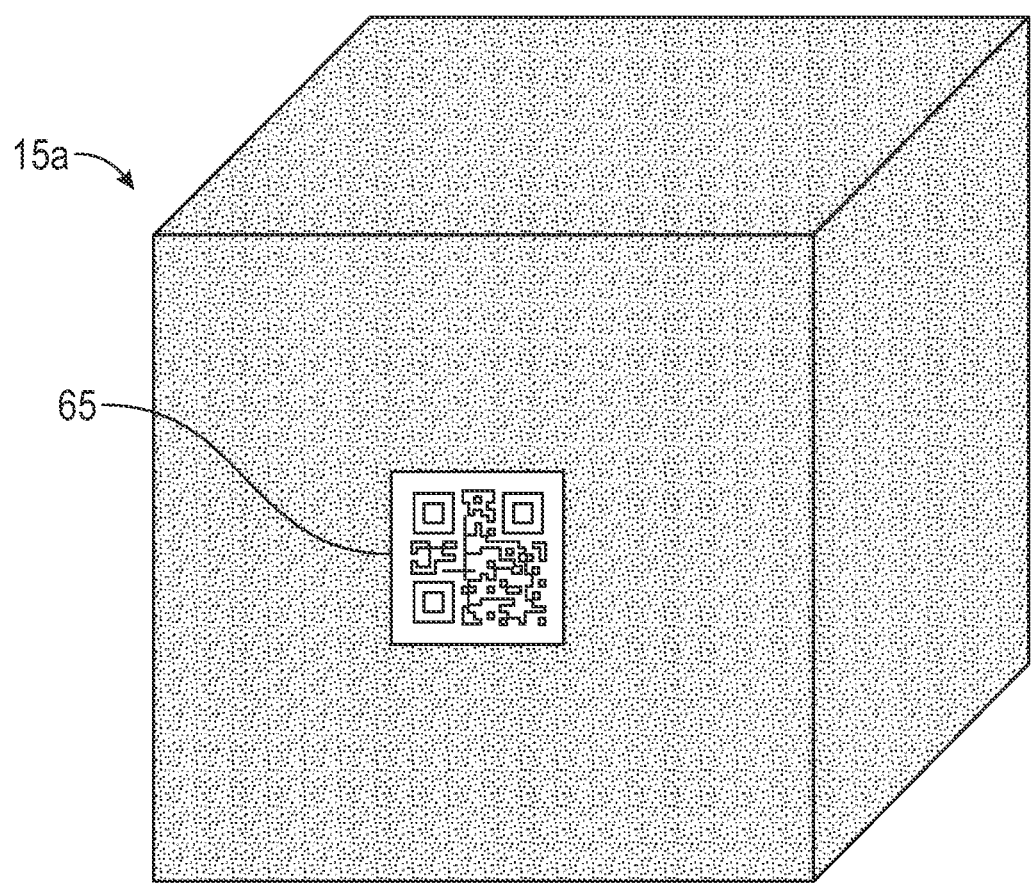
FIG. 2 is an illustration of a floor marker of FIG. 1, according to an example embodiment.

Regarding the floor marker(s) 15, an example of the floor marker 15 is illustrated in FIG. 2. As illustrated, the floor marker 15 includes markings 65 that are capturable by a camera, such as the camera 25b. The markings 65 may include a QR code, as shown in FIG. 2, and/or computer vision distinctive color banding. The markings 65 are not limited to QR codes and instead may be or include SnapTags, an ArUco marker, a WhyCon marker, a WhyCode marker, TRIP circular barcode tags, other types of bar codes such as a high capacity color barcode, data matrix, other type of 2D barcodes, or another fiducial marker such as a portion of a ruler. The markings 65 may be any markings that allow or enable the camera 25b to establish the identity and/or location of the floor marker 15a relative to other floor markers 15 and/or the mobile device 25. The markings 65 allow a mobile device, such as the mobile device 25, to use the relative positions of one or more markers 15 to generate the virtual overlay 38.

Regarding the LED lights 20, in one example, one or more of the floor markers 15 include an LED light. In this example, the camera 25b is capable of establishing the identity and/or location of the floor marker 15 that includes the LED light 20 relative to other floor markers 15 and/or the mobile device 25. In some embodiments, the mobile device 25 uses the relative positions of the LED lights 20 to generate a virtual boundary to be included in the virtual overlay 38. In other embodiments, the system 10 also includes a switch 20' (shown in FIG. 10) that is in communication with one or more of the LED lights 20. As described in more detail below, the switch 20' is selectable and instructs one or more of the LED lights 20 to generate a light signal, which is viewable by the athlete 40 and the camera 25b. The light signal defines a required direction of movement for the athlete 40. Types of lights other than LED lights may be used in the system 10, such as for example halogens, CFL, etc. In some embodiments, the switch 20' includes a foot pedal with a random selector of left or right on a 3-8 second delay. In some embodiments, the switch 20' is not controlled by the mobile application 35 but the mobile application 35 determines the instructed direction by viewing the light signal, as it is seen by the athlete 40. In other embodiments, the switch 20', the lights 20, and/or one or more markers 15 are in communication with the mobile device 25 and/or the mobile application 35, with the mobile application 35 initiating the random selector, controlling the random selector, and/or receiving data regarding the instructed direction from the switch 20'. In some embodiments, the switch 20' and the mobile device 25 and/or the mobile application 35 are in communication via Bluetooth, Bluetooth low energy ("BLE"), or near field communication.

Figure 3:
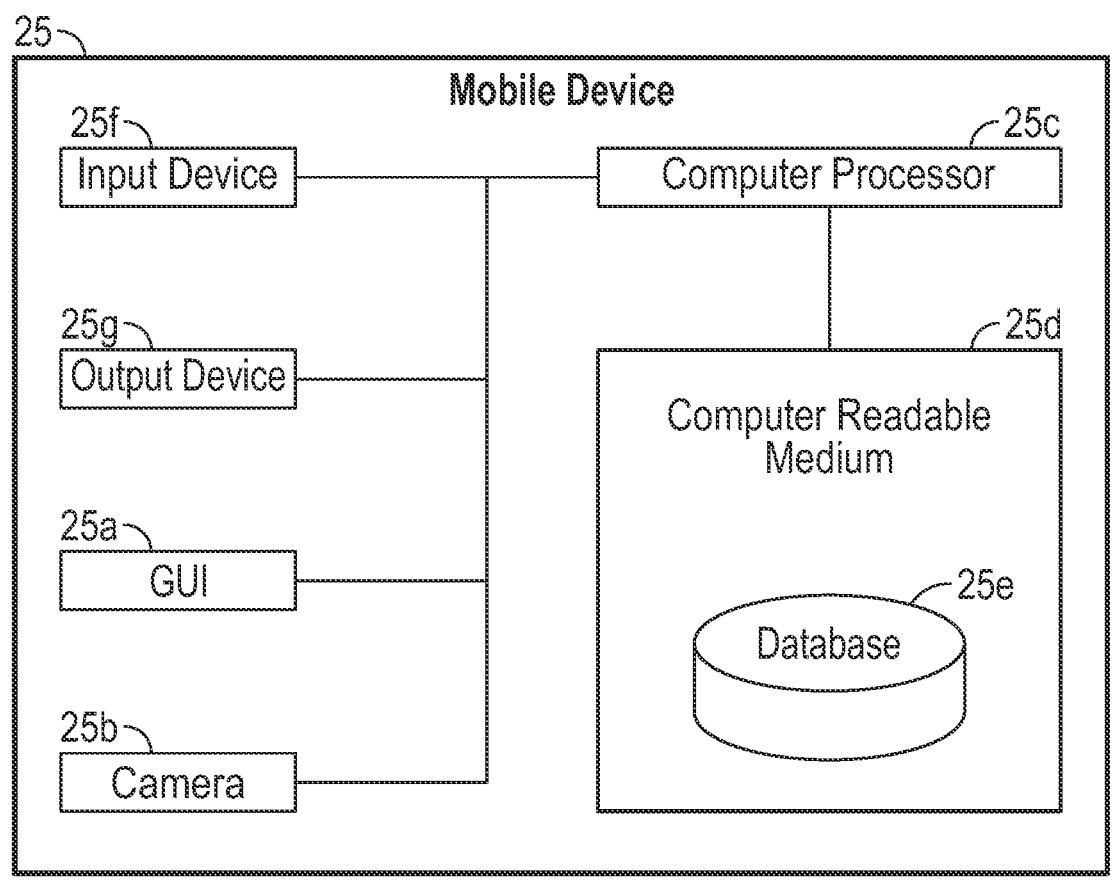
FIG. 3 is a diagrammatic illustration of the mobile device of FIG. 1, according to an example embodiment.

Regarding the mobile device 25, an example embodiment is illustrated in FIG. 3. As illustrated, the mobile device 25 includes the camera 25b, the graphical user interface 25a, a computer processor 25c, and a computer readable medium 25d operably coupled thereto. Instructions accessible to, and executable by, the computer processor 25c are stored on the computer readable medium 25d. A database 25e is also stored in the computer readable medium 25d. Generally, the GUI 25a can display a plurality of windows or screens to the user. The mobile device 25 also includes an input device 25f and an output device 25g. In some embodiments, the input device 25f and the output device 25g are the GUI 25a. However, the input device 25f can also be a microphone in some embodiments and the output device 25g is a speaker. In several example embodiments, the mobile device 25 is, or includes, a telephone, a tablet, a personal computer, a personal digital assistant, a cellular telephone or mobile phone, other types of telecommunications devices, other types of computing devices, and/or any combination thereof. In several example embodiments, the mobile device 25 includes a plurality of remote user devices. In some embodiments, the camera 25b is a depth-perception camera. In some embodiments, the camera 25b includes a first camera and a second camera that are spaced apart from one another to capture different views. The camera 25b is configured to capture the position of one or more floor markers 15. Generally, the mobile device 25 displays the field of view 30 of the camera 25b via the GUI 25a.

Regarding the mobile application 35, performance of an athlete is assessed using the mobile application 35, which captures and measures his or her movements in relation to one or more floor markers 15 and/or one or more LED lights 20. In some embodiments, at least a portion of the mobile application 35 is stored in the computer readable medium 25d of the mobile device 25. Another portion may be stored in the cloud 50 or on a server that is remote from the mobile device 25. In some embodiments, the application 35 includes and/or executes one or more web-based programs, Intranet-based programs, and/or any combination thereof. In an example embodiment, the application 35 includes a computer program including a plurality of instructions, data, and/or any combination thereof. In an example embodiment, the application is written in, for example, Hypertext Markup Language (HTML), Cascading Style Sheets (CSS), JavaScript, Extensible Markup Language (XML), asynchronous Javascript and XML (Ajax), iOS, XCode, Swift, Android for mobile, and/or any combination thereof. In an example embodiment, the application 35 is a web-based application written in, for example, Java or Adobe Flex, which pulls real-time information from the mobile device 25. In some embodiments, the application 35 is or includes a mobile front-end application downloaded on the mobile device 25. In some embodiments, the application 35 accesses the camera 25b, microphone, and/or speaker of the mobile device 25.

Regarding the virtual overlay 38, one embodiment of the virtual overlay includes a virtual shape that is included or laid over the field of view 30 of the camera 25b that is displayed via the GUI 25a. Generally, the shape defines or includes virtual boundaries including virtual planes, which may extend from one floor marker 15 or extend between two or more floor markers 15. In some embodiments, the pixel dimensions of the virtual boundaries are calculated based on the floor marker 15 itself, and where possible, using the distance between two or more floor markers 15.

Regarding the network 60, the network 60 includes the Internet, one or more local area networks, one or more wide area networks, one or more cellular networks, one or more wireless networks, one or more voice networks, one or more data networks, one or more communication systems, and/or any combination thereof.

Figure 4:
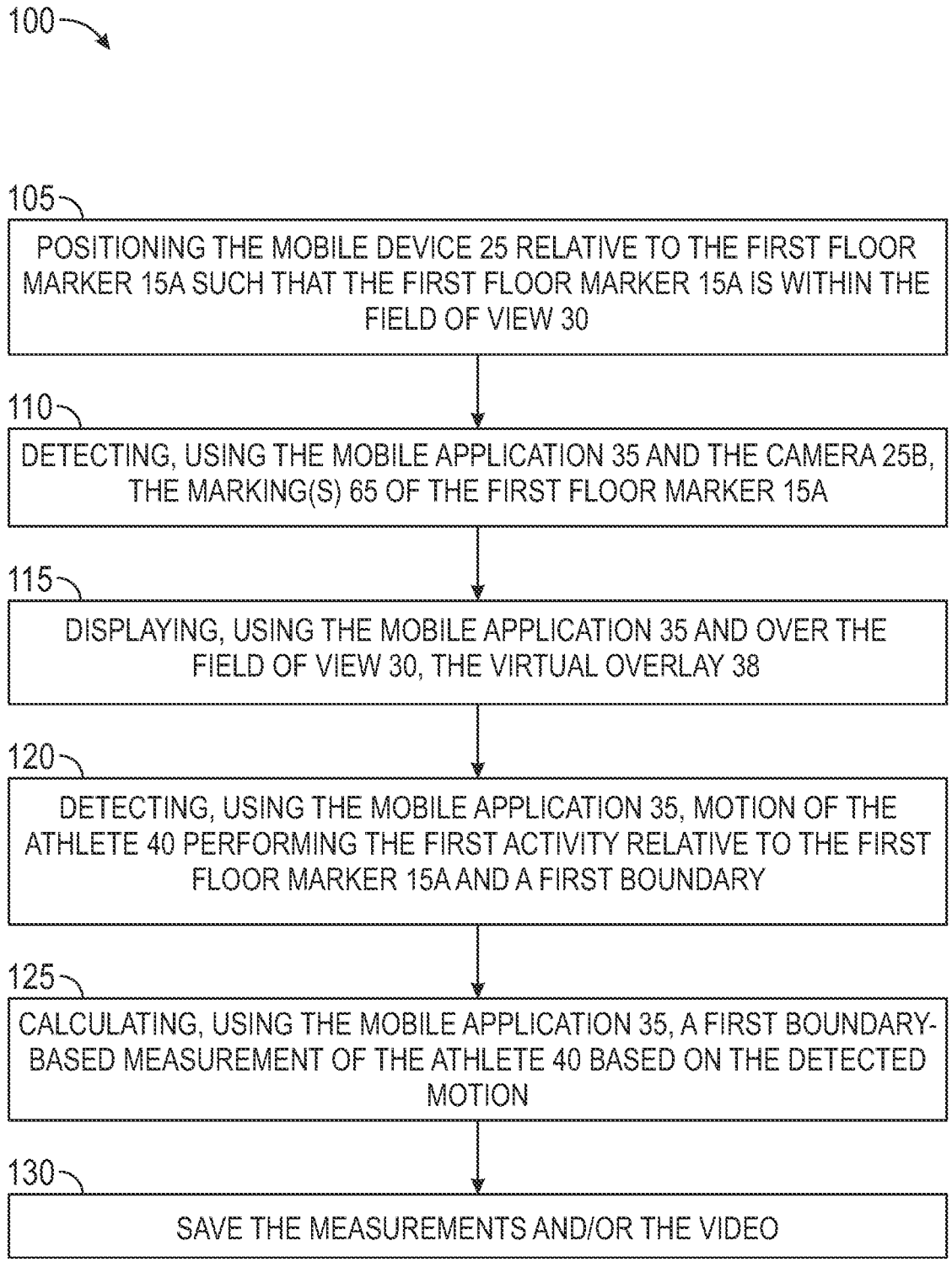
FIG. 4 is a flow chart illustration of a method of operating the system of FIG. 1, according to an example embodiment.

In an example embodiment, as illustrated in FIG. 4 with continuing reference to FIGS. 1-3, a method 100 of operating the system 10 includes positioning the mobile device 25 relative to the first floor marker 15a such that the first floor marker 15a is within the field of view 30 at step 105; detecting, using the mobile application 35 and the camera 25b, the marking(s) 65 of the first floor marker 15a at step 110; displaying, using the mobile application 35 and within the field of view 30, the virtual overlay 38 at step 115; detecting, using the mobile application 35, motion of the athlete 40 performing a first activity relative to the first floor marker 15a and a first boundary at step 120; calculating, using the mobile application 35, a first boundary-based measurement of the athlete 40 based on the detected motion at step 125; and saving the measurements and/or the video of the activity at step 130.

Figure 5:
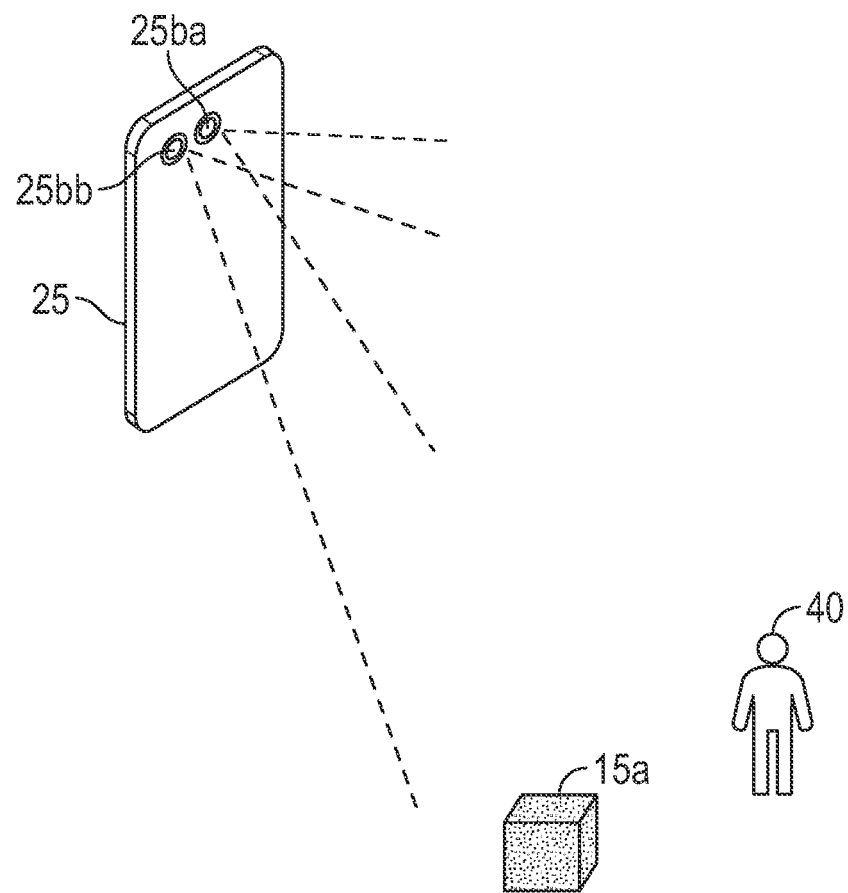
FIG. 5 is an illustration of the mobile device and a floor marker of FIG. 1, according to an example embodiment.

In an example embodiment and at the step 105, the mobile device 25 is positioned relative to the first floor marker 15a such that the first floor marker 15a is within the field of view 30 of the camera 25b. FIG. 5 illustrates the first floor marker 15a that is positioned relative to the mobile device 25 such that the first floor marker 15a is within the field of view 30 of the camera 25b, which in this example includes two cameras 25ba and 25bb. In some embodiments, the mobile device 25 is positioned on a tripod or some other apparatus that allows for the mobile device 25 to remain stationary for a period of time, but this is not illustrated in FIG. 5. The first floor marker 15a defines a real-world first boundary associated with a first activity by which the athlete will be tested. An example of real-world boundaries and activities include a finish line of a race is a boundary associated with the activity of a race. Here, the first activity may be a vertical jump with the first real-world boundary being a target height, a minimum height, and/or a former height to which the athlete should jump. As illustrated in FIG. 5, the real-world boundary is not visible by the athlete and/or the camera 25b without the overlay 38.

Figure 6A:
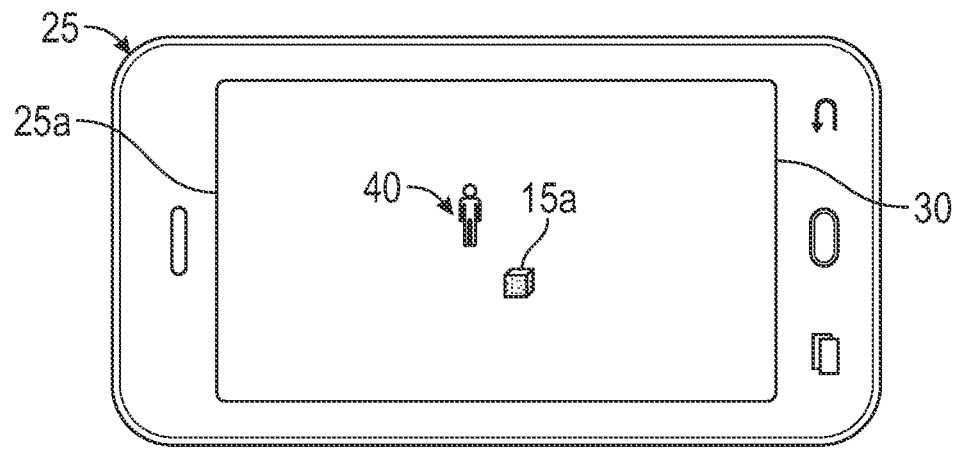
FIGS. 6A-6B are illustrations of the mobile device of FIG. 1, according to an example embodiment.

In an example embodiment and at the step 110, the mobile application 35 and the camera 25b detect the marking(s) 65 of the first floor marker 15a. FIG. 6A provides an illustration of the field of view 30 that includes the first floor marker 15a and the athlete 40. Generally, the mobile application 35 detects the position of the first floor marker 15a relative to the mobile device cameras 25ba and 25bb. As noted above, in some embodiments, the mobile application 35 detects the markings 65, such as, for example, the QR code on each floor marker 15, using the mobile device cameras 25ba and 25bb, in order to detect the relative position of the floor markers 15. The markings 65 may also provide the mobile application 35 additional information such as, for example, the dimensions of the floor marker 15a. For the example provided above regarding the first real-world boundary being a height, the height boundary is defined by the first floor marker 15a because the height is calculated or measured relative to, or based on, the first floor marker 15a. That is, the mobile application 35 first identifies the true size of the first floor marker 15a via the markings 65 or via information already stored in the mobile application 35, compares the perceived size of the first floor marker 15a via the camera 25b to the true size, and then calculates the distance between the first floor marker 15a and the camera 25b and/or other distances relative to the first floor marker 15a (e.g., the height). In some embodiments, the application 35 calculates a distance relative to the first floor marker 15a based on the predetermined size of the marking(s) 65 and using the depth-perception camera 25a.

Figure 6B:
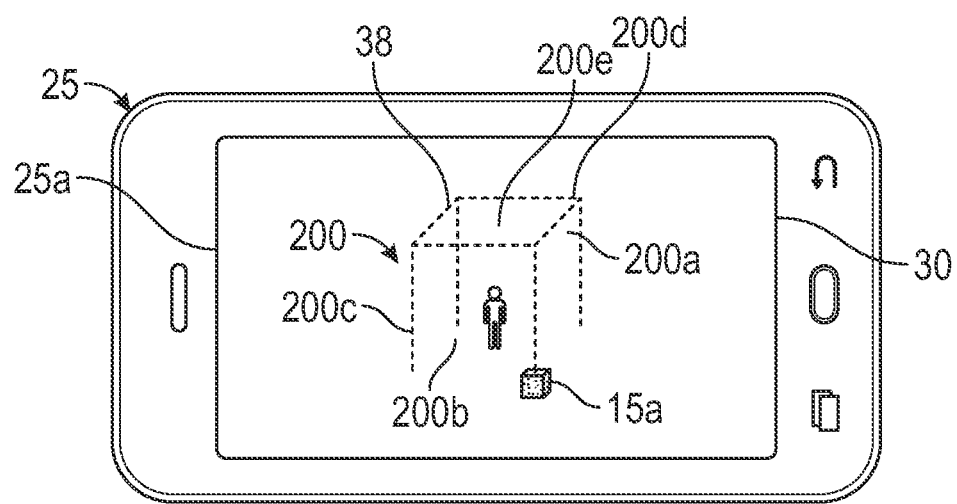

In an example embodiment and at the step 115, the mobile application 35 displays within the field of view 30, the virtual overlay 38. FIG. 6B provides an illustration of the field of view 30 that includes the first floor marker 15a, the athlete 40, and the virtual overlay 38. The virtual overlay 38 is created by the mobile application 35 and includes a visual representation of the first boundary. As illustrated in FIG. 6B, the visual, virtual representation of the first boundary is a box 200. The box 200 includes four vertically extending walls 200a, 200b, 200c and 200d and a horizontal ceiling 200e, with the floor of the box 200 being formed by the physical floor. As shown, the first floor marker 15a defines a corner of the box 200. While a box is illustrated in FIG. 6B, the virtual overlay 38 may include other shapes. For example, the virtual boundary may only include the horizontal ceiling 200e or a single virtual plane. In some embodiments, the virtual overlay 38 may include one or more additional virtual boundaries that are created by extending a virtual plane from a predetermined distance from one of the floor markers 15. In some embodiments, a plurality of virtual boundaries may comprise a perimeter boundary that includes boundaries between outermost floor markers 15. In some embodiments, the virtual overlay 38 may include one or more additional virtual boundaries based on the position of one or more LED lights 20. Additional details and explanation regarding the boundary shapes is provided below.

In an example embodiment and at the step 120, the mobile application 35 detects motion of the athlete 40 performing the first activity relative to the first floor marker 15a and the first boundary, which is the box 200 in this example. For example, if the ceiling 200e is associated with a minimum jump height, a target jump height, a past jump height, etc., and the athlete 40 is jumping toward the ceiling 200e, then the preview 30 will illustrate the performance of the athlete 40 relative to that height in that the athlete 40 will either break the ceiling 200e boundary to exceed the height or barely touch the ceiling 200e to meet the height, or not break the ceiling 200e, thereby falling short of the target/minimum height. Alternatively, the ceiling 200e is movable in response to the performance of the athlete 40. That is, the ceiling 200e may be set at a first predetermined height and, during the test, the athlete 40 jumps toward the ceiling 200e, but instead of the ceiling 200 remaining stationary to the athlete 40, the ceiling 200e moves upward with the athlete's reach (or other portion of the body being tracked for measurement) and remains at the uppermost height that was reached by the athlete to illustrate the athlete's jump height. The mobile application 35 uses the camera 25b to detect motion of the athlete 40.

In an example embodiment and at step 125, the mobile application 35 calculates a first boundary-based measurement of the athlete 40 based on the detected motion. For the example, the measurement is a distance-based measurement, such as, a vertical distance (height) the athlete 40 can achieve when completing a given task (e.g., jumping). The measurement may be another type of distance, such as the length of distance the athlete can cover in a set amount of time. As detailed below, the boundary-based measurement may be a time-based measurement, such as, for example, reaction time, time to move to or from one floor marker 15 to another, or time to complete a given task. Generally, the unit of the boundary-based measurement is dependent upon the activity performed by the athlete 40.

In an example embodiment and at step 130, the mobile application 35 saves the boundary-based measurement and/or video of the activity. In some embodiments, the application 35 uploads the measurements and/or video to the cloud 50. In some embodiments, the mobile application 35 saves the boundary-based measurement and/or the video of the activity in a secure manner such that the integrity of the measurements and video is traceable and/or otherwise un-editable to ensure that the results cannot be changed or edited.

The method 100 and system 10 can be altered in a variety of ways. For example, instead of the visual representation of the first boundary being a box 200, the visual representation of the first boundary may be the wall 200a that extends from the marker 15a. Moreover, the activity is not limited to jumping or an activity that measures a distance. For example and when the first boundary is the wall 200a, the activity may measure the time the athlete 40 is capable of holding a certain position and/or the number of reps performed by the athlete 40 when the athlete 40 remains in a position. For example, one activity requires for the athlete 40 to be positioned in a plank position such that the length of the athlete 40 aligns with the wall 200a, with one hand on one side of the wall 200a and another hand on the other side of the wall 200a. In this example, the mobile application 35 starts counting when the athlete's 40 hand crosses the wall 200a and continues to count the number of reps (i.e., the number of times the athlete's hand crosses the wall 200a) that the athlete 40 can complete in a predetermined period of time. While the movement of a hand is described above, any body marker, biomechanical marker, any other body part, any other marker that tracks the movement of a portion of a user's body, any reliable measurement point, any protocol specific appendage, etc. may be used and tracked. In some embodiments, a body marker includes but not limited to a body or a portion of a body such as a hand, foot, finger, center of a torso, head, arm, leg, etc.

Figure 7A:
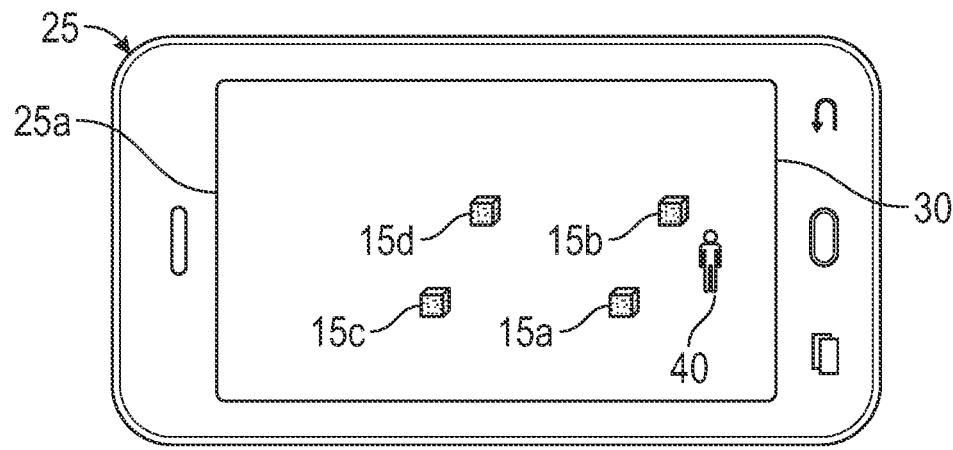
FIGS. 7A, 7B, and 8-10 are illustrations of the mobile device of FIG. 1, according to an example embodiment.
Figure 7B:
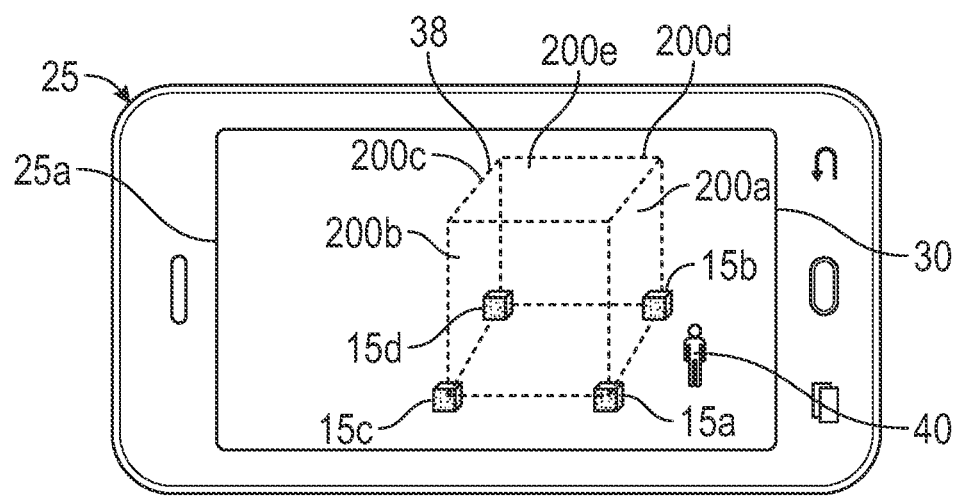

Further, more than one floor marker 15 can be used in the method 100. When multiple floor markers 15 are used in the method 100, the method 100 is similar to when the first floor marker 15a is used. For example, during the step 105, additional floor markers 15 can be positioned within the field of view 30 of the camera 25b. FIG. 7A provides an illustration of the field of view 30 that includes the first floor marker 15a, a second floor marker 15b, a third floor maker 15c, and a fourth floor marker 15d, and the athlete 40. In some embodiments, the additional floor markers 15 can define another boundary associated with the first activity or be used with each other to define one boundary associated with the first activity. When additional floor markers 15 are used in the method 100, the step 110 includes detecting the markings 65 of the additional floor markers 15b-15d. At the step 115, the mobile application 35 displays the virtual overlay 38. FIG. 7B provides an illustration of the virtual overlay 38 when multiple floor markers 15 are used in the method 100. Similar to the overlay in FIG. 6B, the virtual overlay 38 includes the box 200 and the first floor marker 15a defines a corner of the box 200. In FIG. 7B, however, each of the markers 15b, 15c, and 15d defines a corner of the box 200. In this example, the wall 200a is a first boundary and the ceiling 200e is the second boundary. The activity required by the athlete 40 in this example is a distance-step vertical, and requires the athlete to pass through the wall 200a, which is detected by the application 35, and jump toward or through the ceiling 200e. In this example, the height of the jump is detected by the application 35 in a similar manner to the vertical jump described above. In this example, the boundary-based measurement is the highest body distance from the ground.

Figure 8:
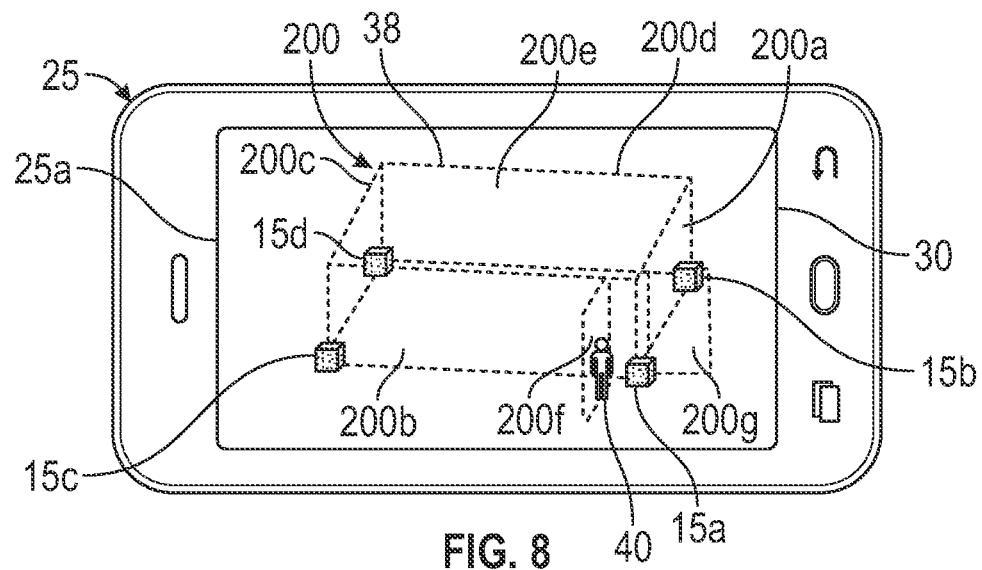

The box 200 can be used in a different type of activity and is not limited to the distance-step vertical activity described above. FIG. 8 provides an illustration that is identical to FIG. 7B except the box 200 of FIG. 8 includes two additional walls 200f and 200g and the box 200 is a rectangular box. The wall 200f is on the same plane as wall 200a except that it does extend between the markers 15a and 15b. Instead, the wall 200f extends from the marker 15a and away from the box 200. Similarly, the wall 200g is in the same plane as 200b but it does not extend between the markers 15a and 15c. Instead, the wall 200g extends from the marker 15a and away from the box 200. The activity associated with the box 200 of FIG. 8 requires the athlete 40 to stay outside of the box 200. In this example, the athlete 40 begins in an area between the walls 200f and 200g and external of the box 200. The boundary-based measurement is the amount of time it takes for the athlete to run around the box 200 in a clock wise rotation for one lap and then back in a counter clock wise rotation, with the application 35 starting a timer as the athlete passes through the wall 200f, ensuring the athlete 40 completes a lap by tracking the athlete 40 passing through the wall 200g after the first clockwise rotation, and then stopping the timer as the athlete passes through that wall 200f after completing the counter clock wise rotation lap. As the athlete 40 is required to stay external of the box 200, the boundary-based measurement may be considered an external boundary based measurement.

Figure 9:
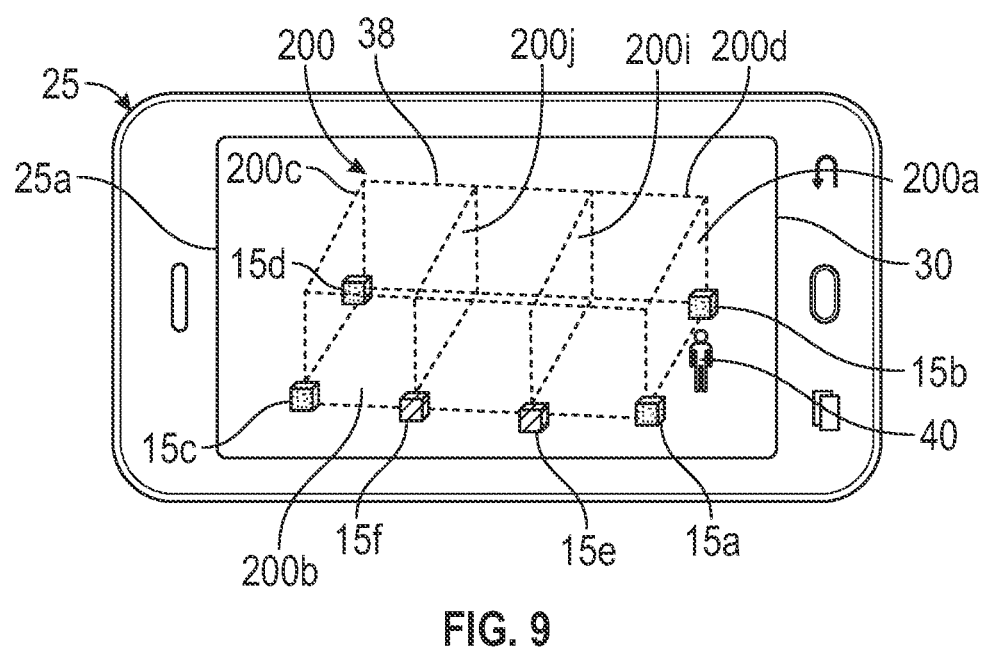

The system 10 can also be used to measure an internal boundary based measurement. FIG. 9 provides an illustration of the field of view 30 that includes the first floor marker 15a, the second floor marker 15b, the third floor marker 15c, the fourth floor marker 15d, a fifth floor maker 15e, and a sixth floor marker 15g, the athlete 40, and the virtual overlay 38. The virtual overlay 38 of FIG. 9 includes a variation to the box 200, with the box 200 includes the walls 200a, 200b, 200c, 200d, and ceiling 200e. The box 200 of FIG. 9 also includes a wall 200i defined by the fifth marker 15e and a wall 200j defined by the sixth marker 15f. As the athlete 40 is required to run through the box 200, the boundary-based measurement may be considered an internal boundary based measurement. In this example, the athlete 40 begins in an area external to the box 200 and near the wall 200a. The boundary-based measurement is the amount of time it takes for the athlete to run through the wall 200a, which starts the clock, and through the wall 200c. Passing through the walls 200i and 200j are splits of the athlete's time. In some embodiments, if the athlete 40 passes through the walls 200b and or 200d, the mobile application 35 considers the athlete 40 disqualified.

Figure 10:
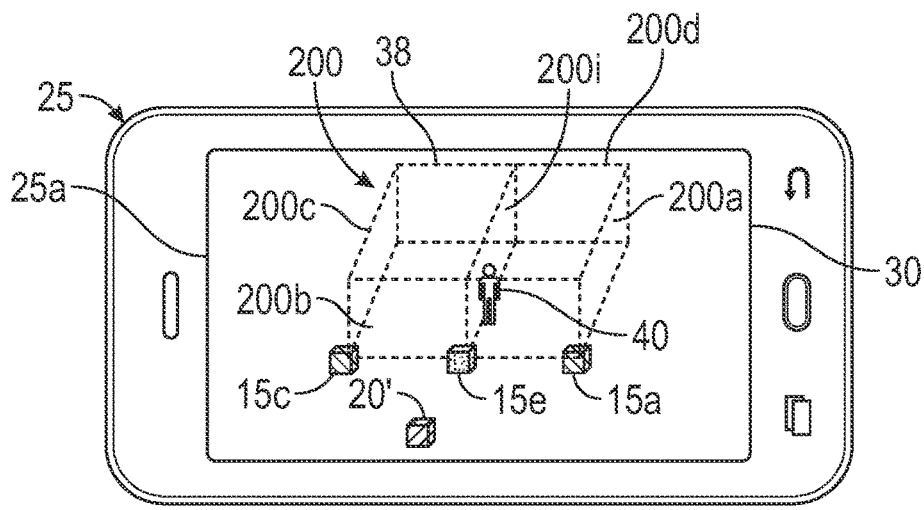

In some embodiments, the LED lights 20 are used to direct the athlete 40 in a specific direction to test the reaction of the athlete 40. FIG. 10 provides an illustration of the field of view 30 that includes the first floor marker 15a that includes a LED light 20, the third floor marker 15c that includes the LED light 20, the fifth floor marker 15e, the switch 20' for the LED lights, the athlete 40, and the virtual overlay 38. The virtual overlay 38 of FIG. 10 includes a variation to the box 200, with the box 200 including the walls 200a, 200b, 200c, 200d, and ceiling 200e. The box 200 of FIG. 10 also includes the wall 200i defined by the fifth marker 15e. The switch 20' may include a foot pedal and may be used to randomly light the LEDs in the first floor marker 15a and third floor marker 15c. The lighting of one of the LED lights 20 is an instruction to the athlete 40 to run toward the plane or wall associated with the LED light that was activated and back to the wall 200i, therefore it may be considered an "out-and-back" test. For example, if the switch 20' lit the LED associated with the wall 200a, the athlete would be timed on how long it took for him or her to cross the wall 200a and then run back to cross the wall 200i. The boundary-based measurement may include the amount of time it takes for the athlete 40 to perform one out-and-back test, but also whether the athlete 40 chose to run toward the correct wall, how many times the athlete 40 chose to run toward the correct wall, or a cumulative score of the total time it took for him or her to run the out-and-back tests. The boundary-based measurement may be any measurement of a variety of measurements. In some embodiments, the LED lights help to define the wall 200a and/or the wall 200c.

In one or more embodiments, the virtual boundaries in a virtual overlay for multiple floor markers may include one or more virtual planes from a predetermined distance from the floor marker, one or more virtual planes between adjacent floor markers, or both. As illustrated in FIG. 10, the wall 200d is a predetermined distance away from the floor markers 15a and 15c and is created without a floor marker being in the plane corresponding to the wall 200d. The inclusion of virtual boundaries between multiple floor markers 15 allows for internal and external boundary-based measurements of athletic performance. For example, in some embodiments such as FIG. 8, a plurality of virtual boundaries may comprise a perimeter boundary including boundaries between outermost floor markers. In one or more embodiments, the virtual boundaries in a virtual overlay for a plurality of floor markers may include one or more virtual planes which are a predetermined distance from the floor markers.

The one or more prespecified virtual boundaries may be based on the activities that the athlete is performing. The activity being performed by the athlete may be one of a plurality of activities that are associated with a sport for which the athlete's performance is being tested. For example, sports such as soccer may require detection of the athlete's movement relative to the inside or outside of the perimeter boundary in order to test the athlete's ability to control the soccer ball.

In some embodiments, the mobile application 35 detects whether the athlete performing an activity did not qualify ("DQ") because the athlete did not perform the activity or test as required. For example, when the athlete must pass through a boundary in order to complete the activity, and when the athlete does not pass through the boundary, then the athlete receives a DQ. In another example, when the athlete must avoid passing through a boundary when completing the activity, and when the athlete does pass through the boundary, then the athlete receives a DQ. Generally, not only does the mobile application 35 detect the DQ, but may also display an indication on a screen that the athlete received a DQ.

In some embodiments, the mobile application 35 detects a DQ because of operator error. For example, and when the athlete is performing an activity, if the field of view moves such that the marker(s) are no longer within the field of view, then the mobile application 35 detects a DQ. Generally, not only does the mobile application 35 detect the DQ, but may also display an indication on a screen that a DQ was identified and/or that a DQ was identified due to operator error.

In some embodiments, the mobile application 35 directs the test administrator in the placement of the floor markers 15, dependent upon the sport selected or activity to be tested. In some embodiments, the mobile application 35 provides feedback to the administrator 45 or user of the mobile device 25 regarding the placement of the floor markers 15. That is, the mobile application 35 is capable of determining the location of the floor markers 15 and providing guidance as to the correct placement of the floor markers. In some embodiments, the mobile application 35 may direct use of one or more floor markers 15 based on a predetermined sport for which an athlete's performance is to be tested. For example, testing for performance related to basketball may only require the use of one floor marker 15, whereas testing for performance related to may require multiple floor markers 15. Each floor marker includes markings 65, such as for example, a QR code, which are capturable by the mobile device camera. In some embodiments, the mobile application 35 may be used to determine whether the floor markers 15 are properly positioned in the field of view 30. In some embodiments, the application 35 provides instructions or other feedback regarding the position of the LED lights 20.

Generally, use of the system 10 and/or implementation of at least a portion of the method 100 improves the process of assessing athletic performance due to the reduction of labor and equipment costs, capture of objective measurements, and simplification of the overall process. Moreover, in some embodiments, use of the system 10 and/or implementation of at least a portion of the method 100 improves the athletic coaching preparation process, such as for example by providing an objective way to compare an athlete to other athletes, or to compare past performances of an athlete to their present performance.

Generally, use of the system 10 and/or implementation of at least a portion of the method 100 results in the display of a virtual overlay over the field of view on a GUI so that the user can see the virtual boundaries created using virtual planes extending from floor markers to other floor markers, LED lights, or for some predetermined distance. This results in the floor markers being properly positioned such that accurate measurements can be calculated using pixel distances between floor markers, such that an improvement to the athletic performance measurement is made by improving measurement accuracy and reliability. As such, the system 10 and/or the method 100 involves a practical application in which the technical field of athletic performance management and/or athletic performance-based coaching is improved.

Moreover, and in some embodiments, the system 10 requires a camera that is configured to capture floor marker data and use known dimensions in order to calculate pixel distances between floor markers and/or LED lights. As such, the mobile device 25 is a particular machine that implements the method 100 in a meaningful way that results in a practical application of virtually measuring athletic performance.

While the method 100 and the system 10 are described as relating to athletic performance in an indoor or outdoor setting, the method 100 and/or the system 10 may be related to any physical performance and is not limited to athletic sports. Instead, the performance measured may be moving in any specified manner through the virtual boundaries, moving an object through the virtual boundaries, etc. Moreover, while the method 100 and the system 10 are described as relating to a sports setting, the method 100 and/or the system 10 may be related to any setting in which physical performance may need to be assessed, and may include physical therapy settings, dance classes, equipment testing, etc. As such, an athlete may be a person or animal.

Using the system 10, the automated collection and storage of the video file to the cloud 50 (directly from the mobile device 25) avoids the storage of the video file in the mobile device 25, thereby improving the functioning of the mobile device 25 by increasing the unused memory available in the mobile device 25. In an example embodiment of the system 10, when a video file is created using the mobile device 25 and the application 35, the video file is not stored in the memory of the mobile device 25, as the video file is automatically uploaded to the cloud 50. Thus, the system 10 improves the functioning of the mobile device 25 because the video file is not stored in the memory of the mobile device 25. Moreover, the mobile application 35 includes a "work on behalf" mode that allows for the test administrator to capture the video on behalf of the athlete 40. In the "work on behalf" mode, the video is not stored on the administrator's device. Instead, data and video are owned by the athlete 40 but captured by the coach/administrator 45, who likely complete the setup of the system 10 and collection of the video on behalf of the athlete 40. In the "work on behalf" mode, the athlete 40 registers for the assessment then transfers capture permission to the administrator 45. The "work on behalf" mode allows for the use of one mobile device 25 to capture videos for different athletes but allows for the upload of that athlete's video to his or her account that is accessible via the cloud 50.

In some embodiments, the protocols and activities described herein are standardized, and therefore, the measurements calculated by the mobile application 35 are used to objectively compare a plurality of athletes regardless of location or testing operator. Moreover, and due to the protocols and activities being measured in a consistent manner, the protocols and activities can be repeated by one athlete over time to measure and/or extrapolate the progress of the athlete. In some embodiments, the mobile application 35, using the protocols and activities, reliably measures athletic performance, provides objective benchmarking for physical development, and/or validates on-field performance and back-to-play parameters. In some embodiments, the mobile application 35 identifies an Improvement Gap associated with an athlete, and the Improvement Gap is derived from the captured measurements. In general, the Improvement Gap illustrates how much change is needed to reach expected performances levels associated with athletes in Division II sports/activities, in Division I sports/activities, in professional sports/activities, etc. In some embodiments, the measurements are instruments for setting an athlete's baseline of athletic performance, which can then be used to set the goal (e.g., Improvement Gap).

Regarding the Improvement Gap, the Improvement Gap can set a performance goal. In some examples, an athlete receives five Improvement Gap calculated values when he or she has five specific activities. Essentially, it is a comparison of an athlete's captured measurement to the expected measurement associated with a particular level of performance. One example involves an athlete that has an Improvement Gap for vertical jump of 0.5" to reach Division II level, 0.8" for achieving Division I level, and 1.6" for professional level of competition. This means that the athlete needs to improve her vertical jump by a half an inch to have a performance level comparable to what would be expected in the Division II range for that protocol; and the athlete needs to improve her vertical jump by 1.6" inches to have a vertical jump comparable to what would be expected at the professional level. If an athlete's 40-yard sprint has an Improvement Gap of −0.48 seconds for Professional, then he needs to reduce sprint time by 0.48 seconds for professional athletic performance. The goal setting for Improvement Gap can be to a competitive level (i.e., varsity, Div II, Div I, pro), a designated percentile level (i.e., 70th percentile), or incremental percentile increase (i.e., next 10th percentile step).

Figure 11:
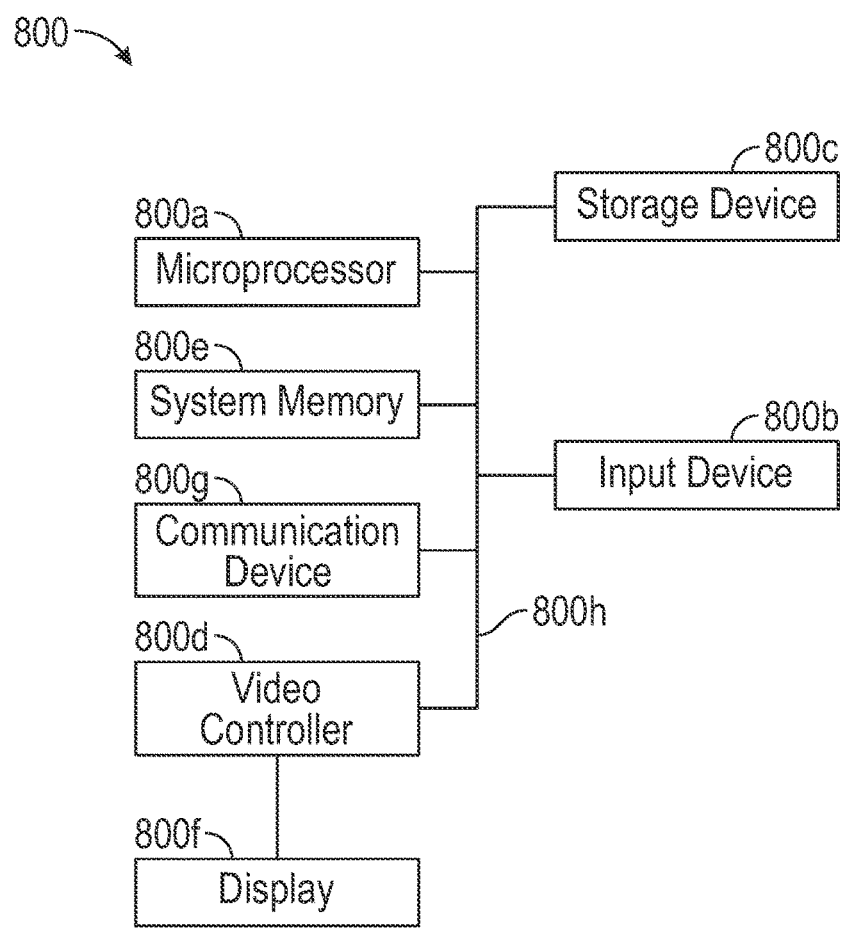
FIG. 11 is a diagrammatic illustration of a node for implementing one or more example embodiments of the present disclosure, according to an example embodiment.

In an example embodiment, as illustrated in FIG. 11 with continuing reference to FIGS. 1-5, 6A, 6B, 7A, 7B, and 8-10, an illustrative node 800 for implementing one or more of the example embodiments described above and/or illustrated in FIGS. 1-5, 6A, 6B, 7A, 7B, and 8-10 is depicted. The node 800 includes a microprocessor 800a, an input device 800b, a storage device 800c, a video controller 800d, a system memory 800e, a display 800f, and a communication device 800g, all interconnected by one or more buses 800h. In several example embodiments, the storage device 800c may include a floppy drive, hard drive, CD-ROM, optical drive, any other form of storage device and/or any combination thereof. In several example embodiments, the storage device 800c may include, and/or be capable of receiving, a floppy disk, CD-ROM, DVD-ROM, or any other form of computer readable medium that may contain executable instructions. In several example embodiments, the communication device 800g may include a modem, network card, or any other device to enable the node to communicate with other nodes. In several example embodiments, any node represents a plurality of interconnected (whether by intranet or Internet) computer systems, including without limitation, personal computers, mainframes, PDAs, smartphones, and cell phones.

In several example embodiments, one or more of the components of the systems described above and/or illustrated in FIGS. 1-5, 6A, 6B, 7A, 7B, and 8-10 include at least the node 800 and/or components thereof, and/or one or more nodes that are substantially similar to the node 800 and/or components thereof. In several example embodiments, one or more of the above-described components of the node 800, the system 10, and/or the example embodiments described above and/or illustrated in FIGS. 1-5, 6A, 6B, 7A, 7B, and 8-10 include respective pluralities of same components.

In several example embodiments, one or more of the applications, systems, and application programs described above and/or illustrated in FIGS. 1-5, 6A, 6B, 7A, 7B, and 8-10 include a computer program that includes a plurality of instructions, data, and/or any combination thereof; an application written in, for example, Arena, HyperText Markup Language (HTML), Cascading Style Sheets (CSS), JavaScript, Extensible Markup Language (XML), asynchronous Javascript and XML (Ajax), and/or any combination thereof; a web-based application written in, for example, Java or Adobe Flex, which in several example embodiments pulls real-time information from one or more servers, automatically refreshing with latest information at a predetermined time increment; or any combination thereof.

In several example embodiments, a computer system typically includes at least hardware capable of executing machine-readable instructions, as well as the software for executing acts (typically machine-readable instructions) that produce a desired result. In several example embodiments, a computer system may include hybrids of hardware and software, as well as computer sub-systems.

In several example embodiments, hardware generally includes at least processor-capable platforms, such as client-machines (also known as personal computers or servers), and handheld processing devices (such as smart phones, tablet computers, personal digital assistants (PDAs), or personal computing devices (PCDs), for example). In several example embodiments, hardware may include any physical device that is capable of storing machine-readable instructions, such as memory or other data storage devices. In several example embodiments, other forms of hardware include hardware sub-systems, including transfer devices such as modems, modem cards, ports, and port cards, for example.

In several example embodiments, software includes any machine code stored in any memory medium, such as RAM or ROM, and machine code stored on other devices (such as floppy disks, flash memory, or a CD ROM, for example). In several example embodiments, software may include source or object code. In several example embodiments, software encompasses any set of instructions capable of being executed on a node such as, for example, on a client machine or server.

In several example embodiments, combinations of software and hardware could also be used for providing enhanced functionality and performance for certain embodiments of the present disclosure. In an example embodiment, software functions may be directly manufactured into a silicon chip. Accordingly, it should be understood that combinations of hardware and software are also included within the definition of a computer system and are thus envisioned by the present disclosure as possible equivalent structures and equivalent methods.

In several example embodiments, computer readable mediums include, for example, passive data storage, such as a random-access memory (RAM) as well as semi-permanent data storage such as a compact disk read-only memory (CD-ROM). One or more example embodiments of the present disclosure may be embodied in the RAM of a computer to transform a standard computer into a new specific computing machine. In several example embodiments, data structures are defined organizations of data that may enable an embodiment of the present disclosure. In an example embodiment, a data structure may provide an organization of data or an organization of executable code.

In several example embodiments, any networks and/or one or more portions thereof may be designed to work on any specific architecture. In an example embodiment, one or more portions of any networks may be executed on a single computer, local area networks, client-server networks, wide area networks, internets, handhelds, and other portable and wireless devices and networks.

In several example embodiments, a database may be any standard or proprietary database software. In several example embodiments, the database may have fields, records, data, and other database elements that may be associated through database specific software. In several example embodiments, data may be mapped. In several example embodiments, mapping is the process of associating one data entry with another data entry. In an example embodiment, the data contained in the location of a character file can be mapped to a field in a second table. In several example embodiments, the physical location of the database is not limiting, and the database may be distributed. In an example embodiment, the database may exist remotely from the server and run on a separate platform. In an example embodiment, the database may be accessible across the Internet. In several example embodiments, more than one database may be implemented.

In several example embodiments, a plurality of instructions stored on a non-transitory computer readable medium may be executed by one or more processors to cause the one or more processors to carry out or implement in whole or in part the above-described operation of each of the above-described example embodiments of the system, the method, and/or any combination thereof. In several example embodiments, such a processor may include one or more of the microprocessor 800*a*, any processor(s) that are part of the components of the system, and/or any combination thereof, and such a computer readable medium may be distributed among one or more components of the system. In several example embodiments, such a processor may execute the plurality of instructions in connection with a virtual computer system. In several example embodiments, such a plurality of instructions may communicate directly with the one or more processors, and/or may interact with one or more operating systems, middleware, firmware, other applications, and/or any combination thereof, to cause the one or more processors to execute the instructions.

This disclosure introduces a method comprising: positioning a mobile device relative to a first floor marker such that the first floor marker is within a field of view of a camera of the mobile device; wherein the first floor marker includes marking(s) capturable by the camera; and wherein the first floor marker defines a first boundary associated with a first activity; detecting, using a mobile application stored within the mobile device and the camera, the marking(s) of the first floor marker; displaying, using the mobile application and over the field of view, a virtual overlay, wherein the virtual overlay includes a visual representation of the first boundary and is based on the marking(s) of the first floor marker; detecting, using the mobile application, motion of an athlete performing the first activity relative to the first floor marker and the first boundary; and calculating, using the mobile application, a boundary-based measurement of the athlete based on the detected motion and the visual representation of the first boundary. In one embodiment, the camera is a depth-perception camera; wherein the marking(s) capturable by the camera have a predetermined size; and wherein the mobile application calculates a distance relative to the first floor marker based on the predetermined size of the marking(s) and using the depth-perception camera. In one embodiment, the first activity requires the athlete to move around, within, or through the first boundary; and wherein the boundary-based measurement is an amount of time that the athlete takes to complete the first activity. In one embodiment, the visual representation of the first boundary comprises a portion of a vertically extending plane; wherein the first floor marker extends within the vertically extending plane; and wherein the first activity requires the athlete to be positioned within the vertically extending plane and cross a body marker through the vertically extending plane. In one embodiment, the visual representation of the first boundary comprises a box; and wherein the first floor marker defines a corner of the box. In one embodiment, the first activity requires the athlete to remain positioned outside of the box while moving around the box. In one embodiment, the box comprises a first vertical wall and a second vertical wall that is parallel to the first vertical wall; and wherein the first activity requires the athlete to pass through the first vertical wall and the second vertical wall. In one embodiment, the box comprises a horizontal ceiling that is perpendicular to each of a first vertical wall and a second vertical wall; and wherein the first activity requires the athlete to jump toward the horizontal ceiling. In one embodiment, the method also includes generating, using a light, a light signal; wherein the light signal is viewable by the athlete; wherein the light signal and the athlete are within the field of view of the camera of the mobile device; and wherein the light signal defines a required direction of movement associated with the first activity; and detecting, using the mobile application and based on the generated light signal and detected motion of the athlete, when the athlete complies with the required direction of movement associated with the first activity. In one embodiment, positioning the mobile device relative to the first floor marker such that the first floor marker is within the field of view of the camera of the mobile device comprises: positioning the mobile device relative to the first floor marker and a second floor marker such that the first floor marker and the second floor marker is within the field of view of the camera; wherein the second floor marker includes marking(s) capturable by the camera; and wherein the second floor marker defines a second boundary associated with the first activity; wherein detecting, using the mobile application stored within the mobile device and the camera, the marking(s) of the first floor marker comprises: detecting, using the mobile application stored within the mobile device and the camera, the marking(s) of the second floor marker; wherein the virtual overlay includes a visual representation of the second boundary; wherein the first activity is measured relative to the first boundary and the second boundary; wherein detecting, using the mobile application, motion of the athlete performing the first activity relative to the first floor marker and the first boundary further comprises detecting, using the mobile application, motion of the athlete performing the first activity relative to the second floor marker and the second boundary; and wherein the boundary-based measurement is relative to the first floor marker and the second floor marker.

This disclosure also introduces a system for virtual measurement, the system comprising: a mobile device comprising: a camera having a field of view; and a graphical user interface; a first floor marker positioned relative to the mobile device such that the first floor marker is within the field of view; wherein the first floor marker includes marking(s) capturable by the camera; and wherein the first floor marker defines a first boundary associated with a first activity; and a non-transitory computer readable medium having stored thereon a plurality of instructions, wherein the instructions are executed with one or more processors so that the following steps are executed: detecting, using the camera, the marking(s) of the first floor marker; displaying, over the field of view, a virtual overlay, wherein the virtual overlay includes a visual representation of the first boundary and is based on the marking(s) of the first floor marker; detecting motion of an athlete performing the first activity relative to the first floor marker and the first boundary; and calculating a boundary-based measurement of the athlete based on the detected motion and the visual representation of the first boundary. In one embodiment, the camera is a depth-perception camera; wherein the marking(s) capturable by the camera have a predetermined size; and wherein the instructions are executed with the one or more processors so that the following step is also executed: calculating a distance relative to the first floor marker based on the predetermined size of the marking(s) and using the depth-perception camera. In one embodiment, the first activity requires the athlete to move around, within, or through the first boundary; and wherein the boundary-based measurement is an amount of time that the athlete takes to complete the first activity. In one embodiment, the visual representation of the first boundary comprises a portion of a vertically extending plane; wherein the first floor marker extends within the vertically extending plane; and wherein the first activity requires the athlete to be positioned within the vertically extending plane and cross a body marker through the vertically extending plane. In one embodiment, the visual representation of the first boundary comprises a box; and wherein the first floor marker defines a corner of the box. In one embodiment, the first activity requires the athlete to remain positioned outside of the box while moving around the box. In one embodiment, the box comprises a first vertical wall and a second vertical wall that is parallel to the first vertical wall; and wherein the first activity requires the athlete to pass through the first vertical wall and the second vertical wall. In one embodiment, the box comprises a horizontal ceiling that is perpendicular to each of a first vertical wall and a second vertical wall; and wherein the first activity requires the athlete to jump toward the horizontal ceiling. In one embodiment, the instructions are executed with the one or more processors so that the following steps are also executed: generating, using the light, a light signal; wherein the light signal is viewable by the athlete; wherein the light signal and the athlete are within the field of view of the camera of the mobile device; and wherein the light signal defines a required direction of movement associated with the first activity; and detecting, based on the generated light signal and detected motion of the athlete, when the athlete complies with the required direction of movement associated with the first activity. In one embodiment, the system also includes a second floor marker positioned relative to the mobile device such that the second floor marker is within the field of view; wherein the second floor marker includes marking(s) capturable by the camera; wherein the second floor marker defines a second boundary associated with the first activity; wherein the virtual overlay includes a visual representation of the second boundary; and wherein the first activity is measured relative to the first boundary and the second boundary; wherein the instructions are executed with the one or more processors so that the following steps are also executed: detecting, using the camera, the marking(s) of the second floor marker; and detecting motion of the athlete performing the first activity relative to the second floor marker and the second boundary; and wherein the boundary-based measurement is relative to the first floor marker and the second floor marker.

In several example embodiments, the elements and teachings of the various illustrative example embodiments may be combined in whole or in part in some or all of the illustrative example embodiments. In addition, one or more of the elements and teachings of the various illustrative example embodiments may be omitted, at least in part, and/or combined, at least in part, with one or more of the other elements and teachings of the various illustrative embodiments.

Any spatial references such as, for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above.

In several example embodiments, while different steps, processes, and procedures are described as appearing as distinct acts, one or more of the steps, one or more of the processes, and/or one or more of the procedures may also be performed in different orders, simultaneously and/or sequentially. In several example embodiments, the steps, processes and/or procedures may be merged into one or more steps, processes and/or procedures.

In several example embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

The phrase "at least one of A and B" should be understood to mean "A, B, or both A and B." The phrase "one or more of the following: A, B, and C" should be understood to mean "A, B, C, A and B, B and C, A and C, or all three of A, B, and C." The phrase "one or more of A, B, and C" should be understood to mean "A, B, C, A and B, B and C, A and C, or all three of A, B, and C."

Although several example embodiments have been described in detail above, the embodiments described are example only and are not limiting, and those skilled in the art will readily appreciate that many other modifications, changes and/or substitutions are possible in the example embodiments without materially departing from the novel teachings and advantages of the present disclosure. Accordingly, all such modifications, changes and/or substitutions are intended to be included within the scope of this disclosure as defined in the following claims. In the claims, any means-plus-function clauses are intended to cover the structures described herein as performing the recited function and not only structural equivalents, but also equivalent structures. Moreover, it is the express intention of the applicant not to invoke 35 U.S.C. § 112 (f) for any limitations of any of the claims herein, except for those in which the claim expressly uses the word "means" together with an associated function.

What is claimed is:

1. A method comprising:
    positioning a mobile device relative to a first floor marker such that the first floor marker is within a field of view of a camera of the mobile device;
        wherein the camera is a depth-perception camera;
        wherein the first floor marker includes marking(s) of a pre-determined size and capturable by the camera; and
        wherein the first floor marker defines a first boundary associated with a first activity;

detecting, using a mobile application stored within the mobile device and the camera, the marking(s) of the first floor marker;
  wherein the mobile application calculates a distance relative to the first floor marker based on the predetermined size of the marking(s) and using the depth-perception camera;
displaying, using the mobile application and over the field of view, a virtual overlay,
  wherein the virtual overlay includes a visual representation of the first boundary and is based on the marking(s) of the first floor marker;
  wherein the visual representation of the first boundary comprises a box; and
  wherein the first floor marker defines a corner of the box;
detecting, using the mobile application, motion of an athlete performing the first activity relative to the first floor marker and the first boundary; and
calculating, using the mobile application, a boundary-based measurement of the athlete based on the detected motion and the visual representation of the first boundary.

2. The method of claim 1,
wherein the first activity requires the athlete to move around, within, or through the first boundary; and
wherein the boundary-based measurement is an amount of time that the athlete takes to complete the first activity.

3. The method of claim 1,
wherein the visual representation of the first boundary comprises a portion of a vertically extending plane;
wherein the first floor marker extends within the vertically extending plane; and
wherein the first activity requires the athlete to be positioned within the vertically extending plane and cross a body marker through the vertically extending plane.

4. The method of claim 1, wherein the first activity requires the athlete to remain positioned outside of the box while moving around the box.

5. The method of claim 1,
wherein the box comprises a first vertical wall and a second vertical wall that is parallel to the first vertical wall; and
wherein the first activity requires the athlete to pass through the first vertical wall and the second vertical wall.

6. The method of claim 1,
wherein the box comprises a horizontal ceiling that is perpendicular to each of a first vertical wall and a second vertical wall; and
wherein the first activity requires the athlete to jump toward the horizontal ceiling.

7. A method comprising:
positioning a mobile device relative to a first floor marker such that the first floor marker is within a field of view of a camera of the mobile device;
  wherein the first floor marker includes marking(s) capturable by the camera; and
  wherein the first floor marker defines a first boundary associated with a first activity;
detecting, using a mobile application stored within the mobile device and the camera, the marking(s) of the first floor marker;
displaying, using the mobile application and over the field of view, a virtual overlay,
  wherein the virtual overlay includes a visual representation of the first boundary and is based on the marking(s) of the first floor marker;
detecting, using the mobile application, motion of an athlete performing the first activity relative to the first floor marker and the first boundary;
generating, using a light, a light signal;
  wherein the light signal is viewable by the athlete;
  wherein the light signal and the athlete are within the field of view of the camera of the mobile device; and
  wherein the light signal defines a required direction of movement associated with the first activity;
detecting, using the mobile application and based on the generated light signal and detected motion of the athlete, when the athlete complies with the required direction of movement associated with the first activity; and
calculating, using the mobile application, a boundary-based measurement of the athlete based on the detected motion and the visual representation of the first boundary.

8. A method comprising:
positioning a mobile device relative to a first floor marker and a second floor marker such that the first floor marker and the second floor marker are within a field of view of a camera of the mobile device
  wherein the first floor marker and the second floor marker include marking(s) capturable by the camera;
  wherein the first floor marker defines a first boundary associated with a first activity; and
  wherein the second floor marker defines a second boundary associated with the first activity;
detecting, using a mobile application stored within the mobile device and the camera, the marking(s) of the first floor marker and the marking(s) of the second floor marker;
displaying, using the mobile application and over the field of view, a virtual overlay,
  wherein the virtual overlay includes a visual representation of the first boundary and is based on the marking(s) of the first floor marker and;
  wherein the virtual overlay includes a visual representation of the second boundary and is based on the marking(s) of the second floor marker;
detecting, using the mobile application, motion of the athlete performing the first activity relative to the first floor marker and the first boundary and motion of the athlete performing the first activity relative to the second floor marker and the second boundary; and
calculating, using the mobile application, a boundary-based measurement of the athlete based on the detected motion, the visual representation of the first boundary, and the visual representation of the second boundary;
  wherein the boundary-based measurement is relative to the first floor marker and relative to the second floor marker.

9. A system for virtual measurement, the system comprising:
a mobile device comprising:
  a camera having a field of view, wherein the camera is a depth-perception camera; and
  a graphical user interface;
a first floor marker positioned relative to the mobile device such that the first floor marker is within the field of view;
  wherein the first floor marker includes marking(s) of a pre-determined size and capturable by the camera; and wherein the first floor marker defines a first boundary associated with a first activity;
and
a non-transitory computer readable medium having stored thereon a plurality of instructions, wherein the instructions are executed with one or more processors so that the following steps are executed:
  detecting, using the camera, the marking(s) of the first floor marker;
  calculating a distance relative to the first floor marker based on the predetermined size of the marking(s) and using the depth-perception camera,
  displaying, over the field of view, a virtual overlay,
    wherein the virtual overlay includes a visual representation of the first boundary and is based on the marking(s) of the first floor marker;
    wherein the visual representation of the first boundary comprises a box; and
    wherein the first floor marker defines a corner of the box;
  detecting motion of an athlete performing the first activity relative to the first floor marker and the first boundary; and
  calculating a boundary-based measurement of the athlete based on the detected motion and the visual representation of the first boundary.

10. The system of claim 9,
  wherein the first activity requires the athlete to move around, within, or through the first boundary; and
  wherein the boundary-based measurement is an amount of time that the athlete takes to complete the first activity.

11. The system of claim 9,
  wherein the visual representation of the first boundary comprises a portion of a vertically extending plane;
  wherein the first floor marker extends within the vertically extending plane; and
  wherein the first activity requires the athlete to be positioned within the vertically extending plane and cross a body marker through the vertically extending plane.

12. The system of claim 9, wherein the first activity requires the athlete to remain positioned outside of the box while moving around the box.

13. The system of claim 9,
  wherein the box comprises a first vertical wall and a second vertical wall that is parallel to the first vertical wall; and
  wherein the first activity requires the athlete to pass through the first vertical wall and the second vertical wall.

14. The system of claim 9,
  wherein the box comprises a horizontal ceiling that is perpendicular to each of a first vertical wall and a second vertical wall; and
  wherein the first activity requires the athlete to jump toward the horizontal ceiling.

15. A system for virtual measurement, the system comprising:
  a mobile device comprising:
    a camera having a field of view; and
    a graphical user interface;
  a first floor marker positioned relative to the mobile device such that the first floor marker is within the field of view;
    wherein the first floor marker includes marking(s) capturable by the camera; and
    wherein the first floor marker defines a first boundary associated with a first activity;
  a light;
  and
  a non-transitory computer readable medium having stored thereon a plurality of instructions, wherein the instructions are executed with one or more processors so that the following steps are executed:
    detecting, using the camera, the marking(s) of the first floor marker;
    displaying, over the field of view, a virtual overlay,
      wherein the virtual overlay includes a visual representation of the first boundary and is based on the marking(s) of the first floor marker;
    detecting motion of an athlete performing the first activity relative to the first floor marker and the first boundary;
    generating, using the light, a light signal;
      wherein the light signal is viewable by the athlete;
      wherein the light signal and the athlete are within the field of view of the camera of the mobile device; and
      wherein the light signal defines a required direction of movement associated with the first activity;
    detecting, based on the generated light signal and detected motion of the athlete, when the athlete complies with the required direction of movement associated with the first activity; and
    calculating a boundary-based measurement of the athlete based on the detected motion and the visual representation of the first boundary.

16. A system for virtual measurement, the system comprising:
  a mobile device comprising:
    a camera having a field of view; and
    a graphical user interface;
  a first floor marker positioned relative to the mobile device such that the first floor marker is within the field of view;
    wherein the first floor marker includes marking(s) capturable by the camera; and
    wherein the first floor marker defines a first boundary associated with a first activity; and
  a second floor marker positioned relative to the mobile device such that the second floor marker is within the field of view;
    wherein the second floor marker includes marking(s) capturable by the camera;
    wherein the second floor marker defines a second boundary associated with the first activity;
    wherein the virtual overlay includes a visual representation of the second boundary; and
    wherein the first activity is measured relative to the first boundary and the second boundary;
  and
  a non-transitory computer readable medium having stored thereon a plurality of instructions, wherein the instructions are executed with one or more processors so that the following steps are executed:
    detecting, using the camera, the marking(s) of the first floor marker;
    detecting, using the camera, the marking(s) of the second floor marker;
    displaying, over the field of view, a virtual overlay,
      wherein the virtual overlay includes a visual representation of the first boundary and is based on the marking(s) of the first floor marker;

detecting motion of an athlete performing the first activity relative to the first floor marker and the first boundary;

detecting motion of the athlete performing the first activity relative to the second floor marker and the second boundary; and calculating a boundary-based measurement of the athlete based on the detected motion, the visual representation of the first boundary, and the visual representation of the second boundary;
  wherein the boundary-based measurement is relative to the first floor marker and the second floor marker.

\* \* \* \* \*